United States Patent [19]
Whisson

[11] Patent Number: 5,425,722
[45] Date of Patent: Jun. 20, 1995

[54] PARENTERAL DEVICE

[76] Inventor: Maxwell E. Whisson, 15 Loftus Street, Nedlands, Western Australia, Australia, 6009

[21] Appl. No.: 960,379
[22] PCT Filed: Jul. 4, 1991
[86] PCT No.: PCT/AU91/00297
  § 371 Date: Jan. 11, 1993
  § 102(e) Date: Jan. 11, 1993
[87] PCT Pub. No.: WO92/00701
  PCT Pub. Date: Jan. 23, 1992

[30] Foreign Application Priority Data

Aug. 20, 1990 [AU] Australia ............... PK1835
Jul. 4, 1991 [AU] Australia ............... PK1008

[51] Int. Cl.6 .................. A61M 5/24; A61M 5/28
[52] U.S. Cl. .................... 604/200; 604/187; 604/195
[58] Field of Search .......... 604/197, 200, 201, 221, 604/227, 198, 232, 213, 165, 110, 164, 263, 187, 197, 86, 204–206, 212, 111, 192–196, 239, 272, 233–235, 89–92; 128/763, 919; 433/89, 90

[56] References Cited

U.S. PATENT DOCUMENTS

| | | | |
|---|---|---|---|
| 3,306,290 | 2/1967 | Weltman | 604/197 |
| 3,563,373 | 2/1971 | Paulson | 206/229 |
| 4,728,320 | 3/1988 | Chen | 604/110 |
| 4,747,831 | 5/1988 | Kulli | 604/110 |
| 4,767,413 | 8/1988 | Haber et al. | 604/198 |
| 4,813,426 | 3/1989 | Haber et al. | 128/763 |
| 4,850,961 | 7/1989 | Wanderer et al. | 604/53 |
| 4,900,310 | 2/1990 | Ogle, III | 604/198 |
| 4,994,042 | 2/1991 | Vadher | 604/165 |
| 5,061,249 | 10/1991 | Campbell | 604/195 |
| 5,248,303 | 9/1993 | Margolin | 604/187 |

FOREIGN PATENT DOCUMENTS

| | | | |
|---|---|---|---|
| 0388169 | 3/1990 | European Pat. Off. | |
| 2240025 | 3/1975 | France | |
| 8808315 | 11/1988 | WIPO | 604/187 |
| 8904141 | 5/1989 | WIPO | |
| 9007349 | 12/1989 | WIPO | |

OTHER PUBLICATIONS

International Preliminary Examination Report, Apr. 8, 1992.

Primary Examiner—C. Fred Rosenbaum
Assistant Examiner—V. Alexander
Attorney, Agent, or Firm—Eckert Seamans Cherin & Mellott

[57] ABSTRACT

A parenteral device having a body slidably supporting a hollow needle. The needle is slidable between a first position in which it is completely retracted within the body and a second position wherein a portion of the needle projects outside of the body. The body further houses a chamber isolated from the needle when the needle is in the first position. Movement of the needle into the second position causes an end of the needle to pierce a wall of the chamber thereby establishing communication between the chamber and needle.

14 Claims, 10 Drawing Sheets

PARENTERAL DEVICE

THIS INVENTION relates to a parenteral device which may take the form of a syringe or similar parenteral dispensing device or a cannula.

In the use of syringes, cannulas and the like which utilise sharp hollow needles there has been significant awareness recently of the dangers which exist as a result of the usage and disposal of these devices. The evidence of such dangers resides in the frequency with which users of the devices are inadvertently pricked. Such an injury can result in the transmission of disease.

As a result of these difficulties users of parenteral devices such as medical clinics, hospitals and the like apply very stringent procedures in the storage, use and disposal of parenteral devices which utilise sharp needles. However, despite such very stringent procedures it is a regular occurrence for professional users to be inadvertently pricked.

In addition there is a need for the parenteral devices such as syringes to be generally available to patients for the self application of parenteral agents to those patients. This is particularly the case where patients are required to regularly administer to themselves agents which must be regularly administered and can only be administered by hypodermic or intravenous injection. As a result it is necessary for such users to have readily available to them ampoules which store the active agent, syringes and needles. When administration is required the users must assemble the syringe, fill the syringe with the parenteral agent, inject themselves with the agent and then dispose of the syringe and needle in a responsible manner. In addition when administration is required the user can often be experiencing stress which can make the tasks of assembling the syringe, filling the syringe, injection and disposal of the syringe a difficult exercise.

In addition as a result of the use of illegal drugs which are generally administered intravenously by utilisation of syringes there has arisen considerable difficulty as a result of the inappropriate disposal of such syringes by the users of illegal drugs and the increased danger of transmission of disease due to such syringes being carelessly disposed of or used by a second person.

It is an object of this invention to at least partially alleviate the difficulties that are created by the use and disposal of conventional syringes by professionals, patients and drug users.

In one form the invention resides in a parenteral device comprising a body, said body having a chamber supporting a hollow needle having a pointed one end formed with a first aperture, said needle having a second aperture inward of the first aperture, said needle being supported in the body for slidable movement between a first position and a second position wherein said first position comprises said needle being fully accommodated within the body and said second position comprises said one end of the said needle extending beyond the body, wherein said needle in its movement from the first position to the second position is capable of piercing the chamber and causing the second aperture to be in open communication with the interior of the chamber when the needle is at the second position to allow for flow of parenteral fluid between the chamber and the first aperture through the second aperture.

According to a preferred form of the invention the chamber of the parenteral device comprises a sealed chamber which is variable in volume whereby on the needle being moved to its second position the parenteral agent which is stored within the chamber can be injected by a reduction of the volume of the chamber, In this regard the ejection of the parenteral fluid from the chamber may be effected by the collapse of the chamber as a result of a resilient biassing force such that on the needle being moved to its second position the parenteral agent is automatically ejected through the needle.

In addition means may be provided in the body to interact with the needle such that on the needle having been moved from the first position to the second position its subsequent movement from the second position to the first position will lockingly retain the needle in the body to prevent re-use of the parenteral device and/or the inadvertent extension of the needle from the device once disposed.

According to a further preferred feature of the invention the unused parenteral device when having the needle accommodated in its first position substantially isolates the needle from the environment exterior to the parenteral device whereby on movement of the needle initially from the first position to the second position the one end of the needle pierces a wall or membrane in the body to become exposed.

According to one form of the invention the second aperture in the needle is provided in a portion of the needle which is offset from the main body of the needle and which is caused to extend from the body and is arranged such that the second aperture is provided in the end of the offset portion which is caused to pierce the chamber on its movement to the second position of the needle, This can be effected by forming the needle into a "hook like" shape where the hooked portion of the needle which accommodates the second aperture is of a shorter length than the main body of the needle and is directed substantially parallel to the main body of the needle.

The invention will be more fully understood in the light of the following description of several specific embodiments.

The description is made with reference to the accompanying drawings of which.

The first embodiment of the invention which is shown at FIGS. 1, 2, 3, 4 and 5 comprises a device which enables the storage of a parenteral medium with a means of dispensing that parenteral medium by injection when desired.

Figure 3:
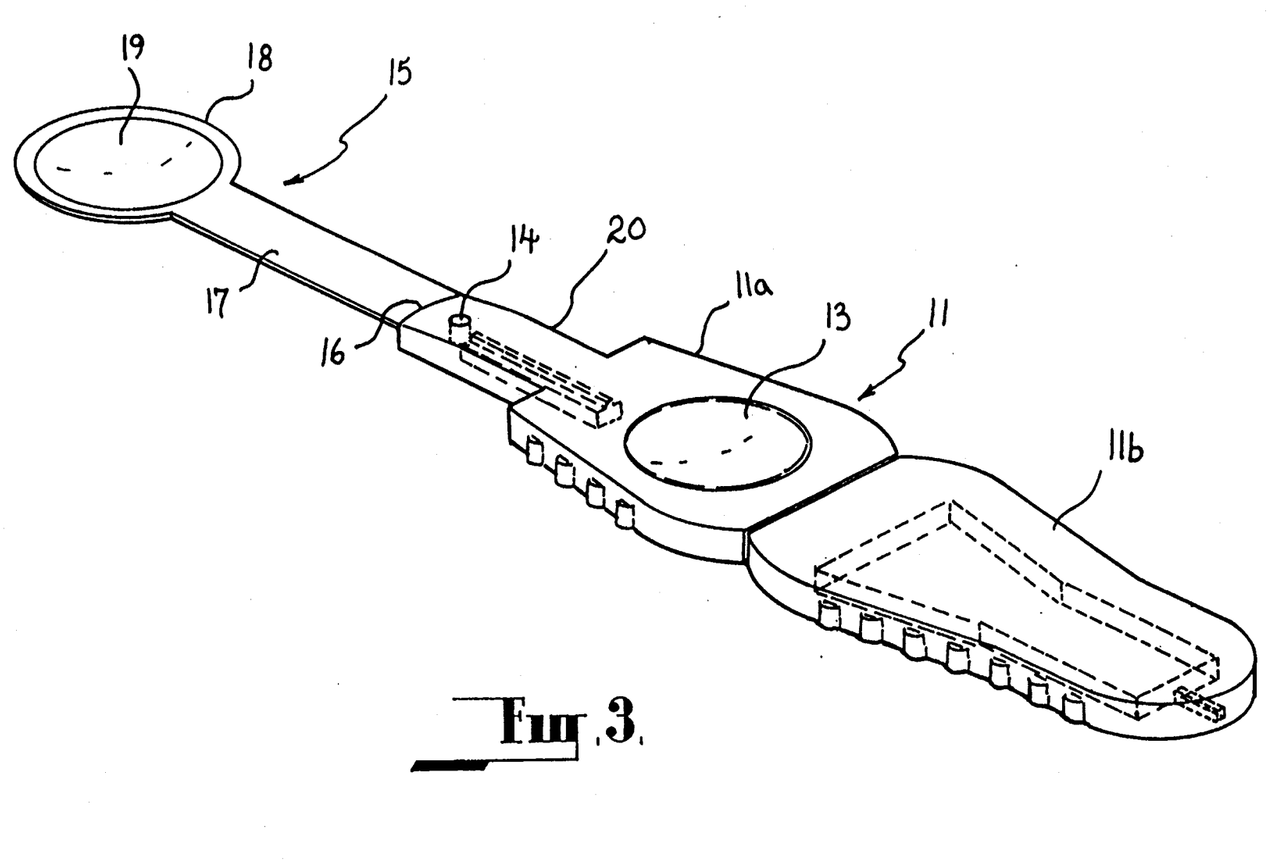
FIG. 3 is an isometric view of the moulding which forms the body of the embodiment first.
Figure 4:
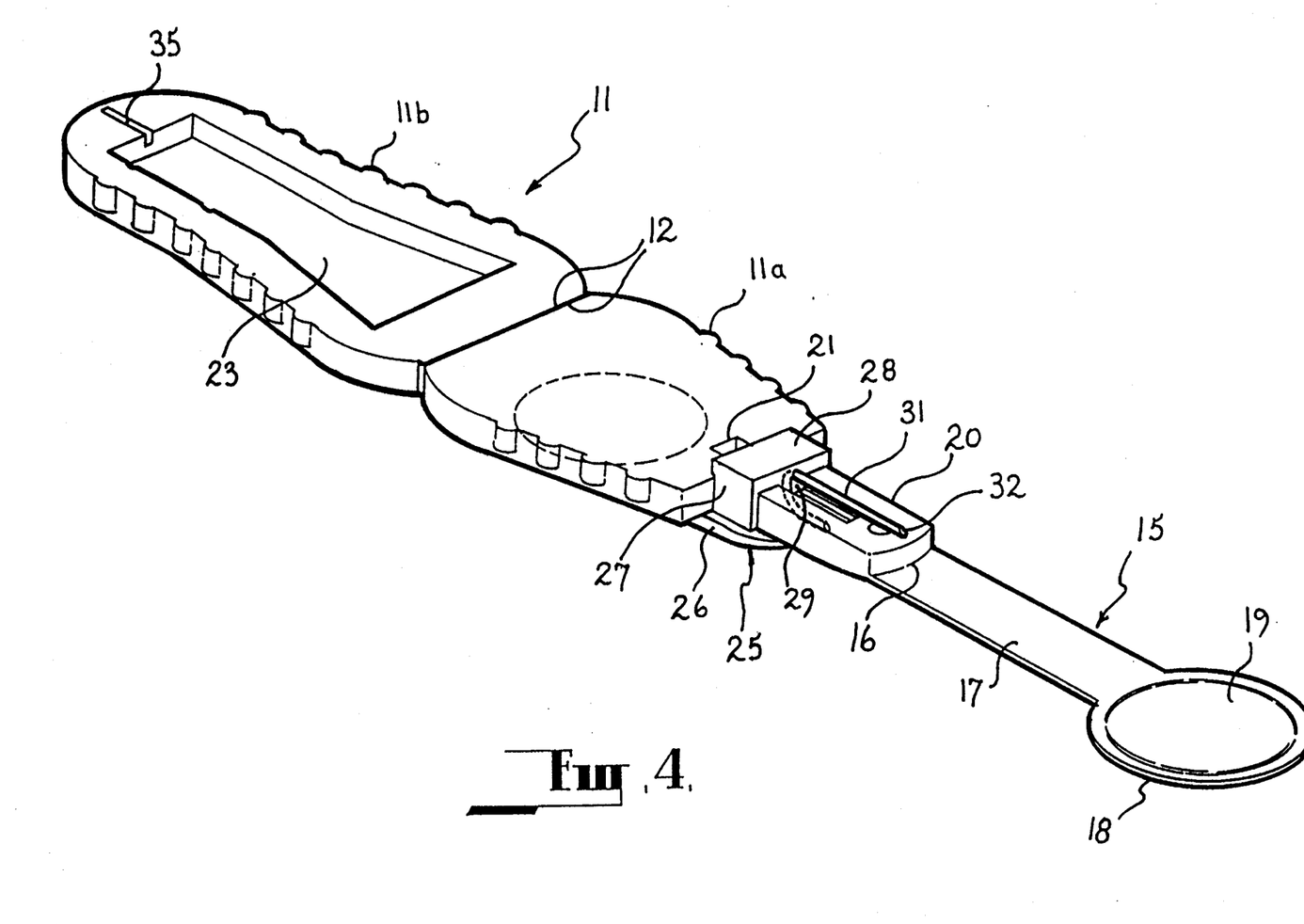
FIG. 4 is an isometric inverted view of the moulding shown at FIG. 3 showing the handle and needle in position.
Figure 5:
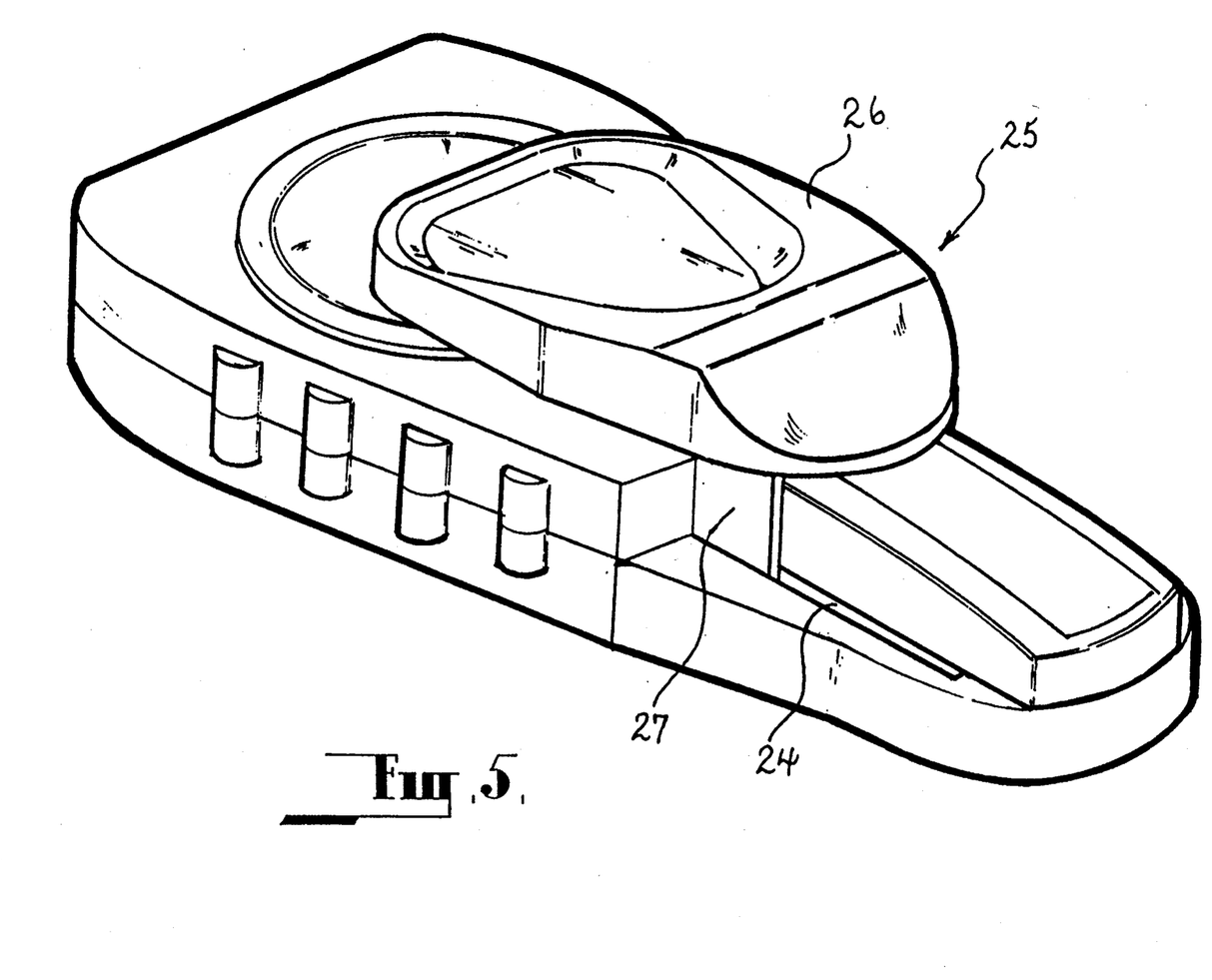
FIG. 5 is an isometric view of the embodiment with the needle in the first position.

The embodiment comprises a moulding of plastics material which defines a body 11 which is formed as two parts 11a and 11b. The body 11 is formed by a pressure injection moulding technique or like technique and has as shown in FIGS. 3 and 4 the two separate parts which are hingedly interconnected at their rear edges 12. In forming the parts 11a and 11b suitable retention means (not shown) are moulded into the opposing faces such that when opposing faces of the parts 11a and 11b are brought into face to face engagement the retention means are inter-engaged to lockably retain the two parts together.

One part 11a of the body is formed on one exterior face with a concave depression 13 which is located towards the rear side of the one part and a recess 14 which is located towards the forward side of the housing.

In forming the housing the one part 11a of the housing also has integrally formed with it, by the moulding technique, a thin laminar member 15 which extends from the forward edge 16 of the one part 11a adjacent its external face. The laminar member 15 is formed as a parallel sided strip which extends from the front edge and terminates with a circular portion 18 having a central portion 19 of complementary configuration to the concave depression 13 which is provided on the one part. In assembling the body the laminar member 15 is laid over the exterior face of the one part 11a and it is welded or similarly fixed around its edges to the one part 11a to define a sealed reservoir between itself and the exterior face of the one part 11a. The sealed space comprises the volume of the concave depression 13 and the recess 14 together with the space that is defined between the laminar member 15 and the exterior face of the one part 11a. The central portion 17 of the laminar member is formed of a thickness such that it has resilient flexibility and has a conformity to the depression 13 when placed over the depression. On application of fluid pressure to the interior of the space defined between the one part 11a and the opposed face of the laminar member 15, by the introduction of the parenteral agent the space can be expanded.

The one part 11a is formed at its forward end with a tongue like portion 20 which accommodates the recess 14, has substantially parallel sides and which is overlaid by the parallel sided strip 17 of the laminar member 15. The under face of the tongue like portion is formed with a groove 21 which extends for a portion of the length of the tongue 20 but stops short of the recess 14. The lower face of the groove 21 is formed with a central narrower groove 22 which has the same length as the main groove 21. The inner face of the other part 11b of the body which is to be disposed in opposed relation to the groove 20 is formed with a recess such that a substantial portion of the upper part 11b defines a hollow space 23 on engagement with the one part 11a. A portion of the hollow space which lies opposite the tongue of the one part when the two parts are inter-engaged is slightly wider than the tongue to provide a slot shaped aperture 24 to each side of the tongue (see FIG. 5).

The tongue 20 of the one part 11a of the body supports a handle 25 which is formed with a handle portion 26 which is slidably received over the exterior face of the tongue 20 and is formed on its underside with a pair of parallel webs 27 which are located to each side of the tongue 20 and are received in the slot shaped apertures 24 which are formed between the tongue 20 of the one part 11a and the hollow space 23 provided on the other part 11b. The parallel webs are interconnected by a support member 28 which has a substantially T-shaped profile where the leg 29 of the section is received in the groove 21 provided on the underface of the one part 11a for movement along the groove. The support provides support for a hook shaped needle 30 having a main body portion 31 which extends forwardly from the support parallel to the underface of the one part 11a of the body. The main body is formed with a first aperture 32 in its free end which comprises the one end of the needle. The hook portion 33 of the needle extends substantially parallel to the main portion 31 and is formed with a second aperture 34 in the other end of the needle. Both the one end and the other end of the needle are pointed.

The hook portion 33 of the needle 30 is slidably received within the minor groove 22 provided at the base of the groove 21 which is formed on the inner face of the one part 11a. The forwardmost end of the minor groove 22 terminates short of the recess 14 such that it is separated from the recess 14 by a thin wall. The inner face of the other part 11b towards the forward end of the space 23 provided in that part is also formed with a third groove 35 which terminates short of the front face Such that a thin wall is provided between the end of the third groove 35 and the front face of the one member.

Figure 1:
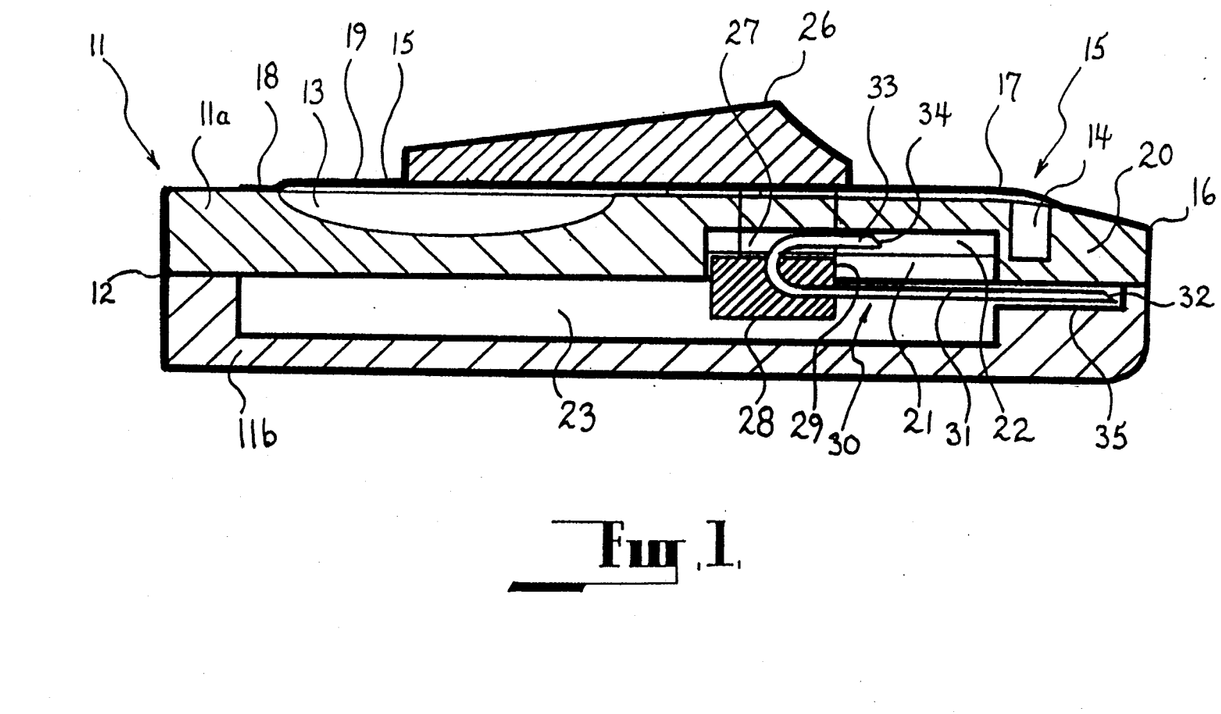
FIG. 1 is a sectional side elevation of the first embodiment showing the needle in the first position.
Figure 2:
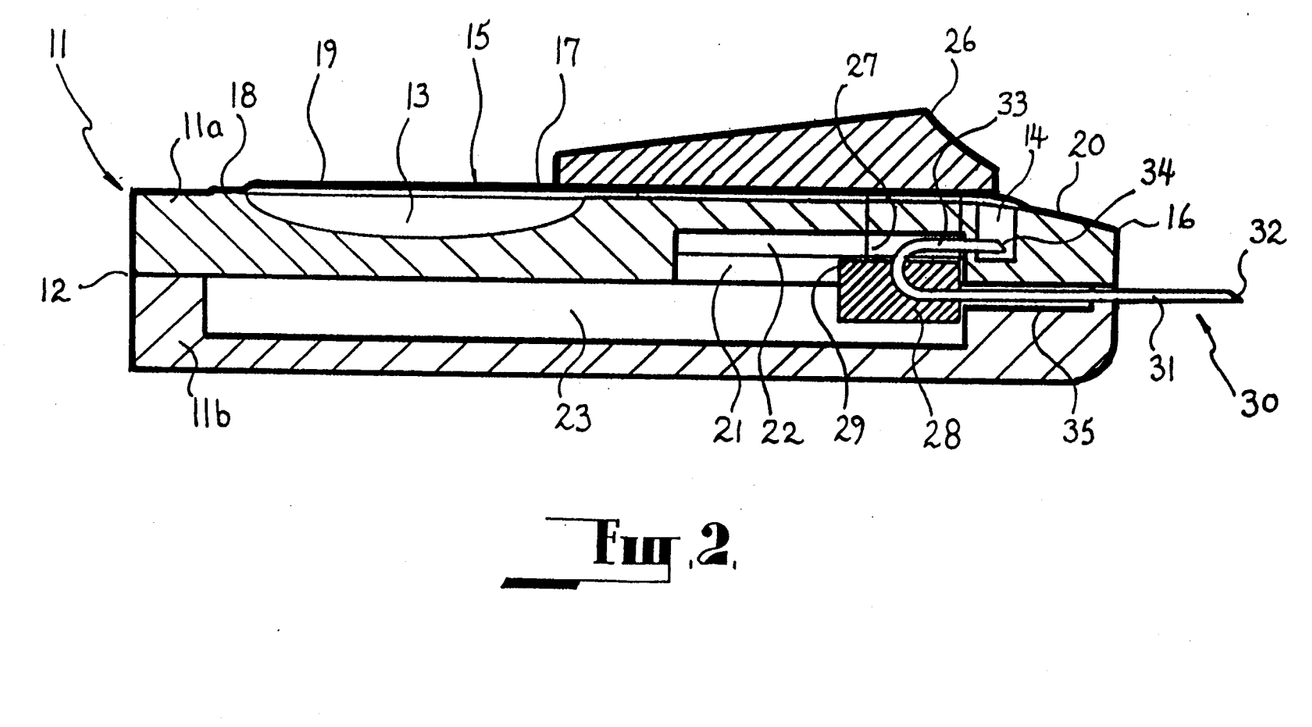
FIG. 2 is a sectional side elevation of the first embodiment showing the needle in the second position.

As a result of the engagement of the handle 25 over the tongue 20 the handle 25 is capable of slidable movement along the tongue 20 from a first position as shown at FIG. 1 where the support 20 is located towards the rear end of the groove 21 provided in the inner face of the one part 11a and a second position shown at FIG. 2 where it is located adjacent the front face of the groove. On movement of the handle from the first position to the second position the one end of the needle 30 pierces the thin wall provided at the front end of the third groove 35 to become exposed to the exterior of the body. The other end of the needle pierces the wall between the front end of the minor groove 21 and the recess 14 when the handle is almost at its second position. The piercing of the recess by the hook portion 33 then provides communication between the first aperture 32 at the one end of the needle and the volume defined by the chamber which was formed between the outer face of the one part 11a and the laminar member 15. As a result there is a flow of fluid from the chamber into the second aperture 34 through the needle and out of the first aperture 32 on the volume of the chamber being reduced. The reduction of the volume in the chamber can be effected by the application of pressure by the central portion 19 of the laminar member which is located above the depression 13 provided in the body due to the resilient biassing caused by the expansion of the central portion when the chamber is filled. Such pressure can also be applied by a finger or a thumb.

As stated if desired the central portion 19 of the laminar member 15 may have its own resilience and be biassed to a minimum volume position whereby on the second end 34 of the needle piercing the recess 14 the Chamber will collapse under the resilient pressure applied by the central portion 19 to cause the injection of parenteral medium into the tissue from the one end of the needle. In such an instance the insertion of the one end of the needle into the tissue is effected while the needle is being moved from its first to its second position on the body 11. This can be effected by locating the front end of the body 11 adjacent to the skin of the patient and then moving the needle in a single action from the first position to the second position during which phase it will enter the tissue of the patient. Alternatively the central portion 19 of the laminar member 15 may have a resilience whereby it is biassed to a maximum volume position which will require the application of thumb or finger pressure to effect injection of the parental agent into the tissue of the patient.

On completion of the injection of the parental medium the needle is then moved to its first position by rearward movement of the handle in the body. Once the needle has been safely located into its first position whereby the one end of the needle is safely accommodated within the body the device may be disposed of with little likelihood of there being any inadvertent pricking of any person who comes into contact with the device. If desired a locking means may be provided between the body and the handle which will engage the handle on it being removed rearwardly to the first position and which will positively lock the handle into its first position. Alternatively, a biassing means may be provided between the handle and the body which biasses the handle to the first position whereby movement of the handle from the first to the second position requires positive movement against the biassing force and on the removal of the application force the biassing force will cause the retraction of the handle and needle.

To fill the chamber defined between the one part 11a and the laminar member a hollow needle can be caused to pierce the one part to enter the depression 13 or recess 14 and a parenteral agent is injected into the chamber. If the body is formed of a suitable resiliently flexible plastics material the hole caused by the hollow needle can be self sealing. Alternatively the hole can be sealed by wadding or by application of a sealant or by gluing.

The embodiment provides a means of safely storing a parenteral agent in association with a needle whereby when it is required to effect injection of the parenteral medium into tissue of the patient there is no requirement for the patient to install the needle separately to the body of the syringe, nor to fill the syringe with the parenteral agent before the agent can be applied as is the conventional technique. Furthermore, prior to use and subsequent to the use the needle is stored in a position where it is not accessible for any inadvertent pricking of any user or person who may handle the syringe.

Figure 6:
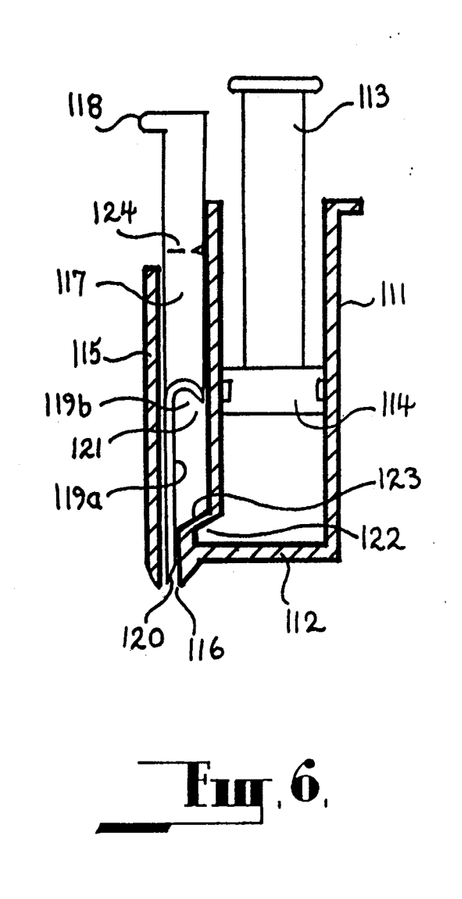
FIG. 6 is a schematic side elevation of the second embodiment showing the needle in the first position.
Figure 7:
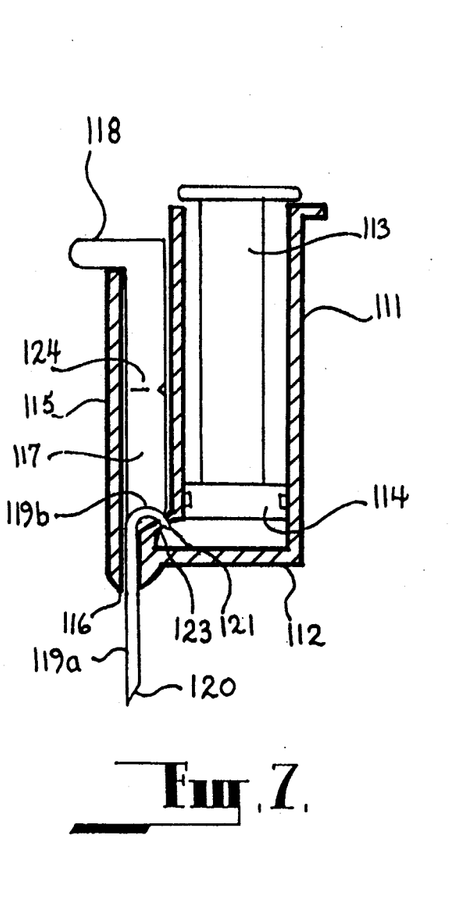
FIG. 7 is a schematic sectional side elevation of the second embodiment showing the needle in the second position.
Figure 8:
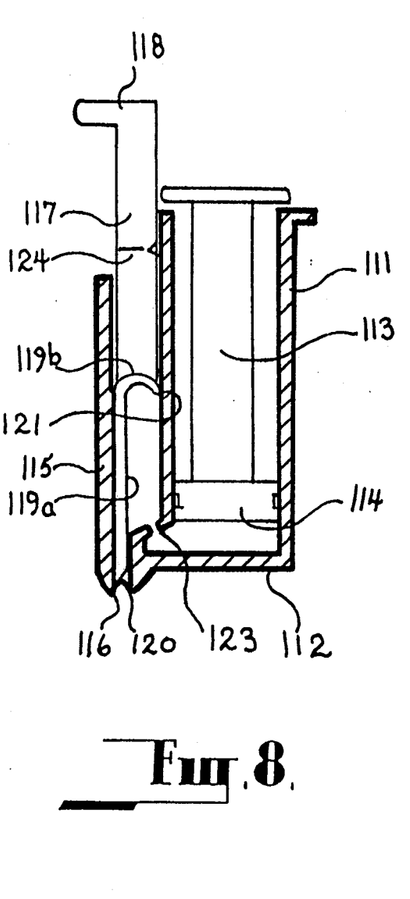
FIG. 8 is a sectional side elevation of the second embodiment showing the needle in the first position having been moved from that position to the second position.

The second embodiment of the invention which is shown very schematically at FIGS. 6, 7 and 8 is directed to an application of the invention to a substantially conventional syringe. The syringe comprises a substantially hollow cylindrical body 111 having a closed end 112 which accommodates a plunger 113 having a piston 114 at its inner end which is slidably and sealingly received in the bore of the cylinder. The syringe is associated with a tubular member 115 which is fixed to the side of the cylindrical body, is substantially parallel thereto and has an opening 116 adjacent the closed end 112 of the cylindrical body. The tubular element receives a rod shaped member 117 having a handle 118 at its outer end and which supports at its inner end a hook shaped hollow needle 119. The main body 119a of the needle accommodates the pointed first end 120 of the needle which lies adjacent the opening 116 when the rod shaped member and needle are in the retracted first position in the tubular member 115. The hook shaped portion 119b of the needle provides the second end 121 of the needle which is also pointed.

The lower portion of the cylinder adjacent the closed end 12 is formed with a transversely directed portion 122 which defines an extension of the space defined by the bore of the cylinder and is formed with a transverse wall 123 which extends into the tubular member to intersect across the path of the second end 121 of the needle as the needle is moved from its first position at which the main body 119a accommodated within the tubular member, to its second position as shown at FIG. 7, at which the main body of the needle 119a of the needle and the first end 120 of the needle is exposed from the body. Towards the end of such movement the second end 121 of the needle will engage the transverse wall 123 and pierce that wall such that the aperture provided in the second end of the needle comes into open communication with the interior of the chamber defined by the cylindrical body. On manipulation of the plunger parenteral fluid can be drawn into the cylindrical body by withdrawing the plunger from the cylindrical body or the parenteral fluid can be expelled from the chamber through the one end of the needle by moving the plunger into the cylindrical body.

As a result of the second end 121 of the needle piercing the transverse wall 123 it is caused to be deformed or bent outwardly. On completion of the use of the syringe the needle is then withdrawn to its first position by utilisation of the handle 118 provided on the outer end of the rod member 117. However, due to the deformation of the hook portion 119b of the needle the other end of the needle is caused to be brought into engagement with the interior wall of the tubular member. As a result of the deformed orientation of the needle the hook shaped portion is able to slide rearwardly into the tubular member with the application of some additional effort to the handle 118 but the interference effected by the engagement of the second end 121 of the needle with the side wall of the tubular member prevents further movement of the needle from the first position and thus the needle is locked in the first position. Furthermore the rod member may be formed with a line of weakness 124 whereby it can be broken along that line of weakness and prevent further utilisation of the handle 18 to cause movement of the needle.

As a result of the second embodiment a syringe is provided whereby the interior of the chamber of the syringe will remain isolated until such time as the syringe is required to be used either to draw parenteral fluid into or for the injection of a parenteral agent which is stored within the chamber. The movement of the needle to its extended second position such that the syringe can be used for the injection of the parenteral agent into tissue of the body or withdrawal of a parenteral agent from the tissue of the body can be readily achieved in a simple manual function. Finally on completion of the usage of the device the needle can be retracted to a first position at which it is not accessible and the needle can be locked in that position to prevent any further inadvertent use of the syringe or inadvertent pricking of any person who may come into contact with the syringe.

Figure 9:
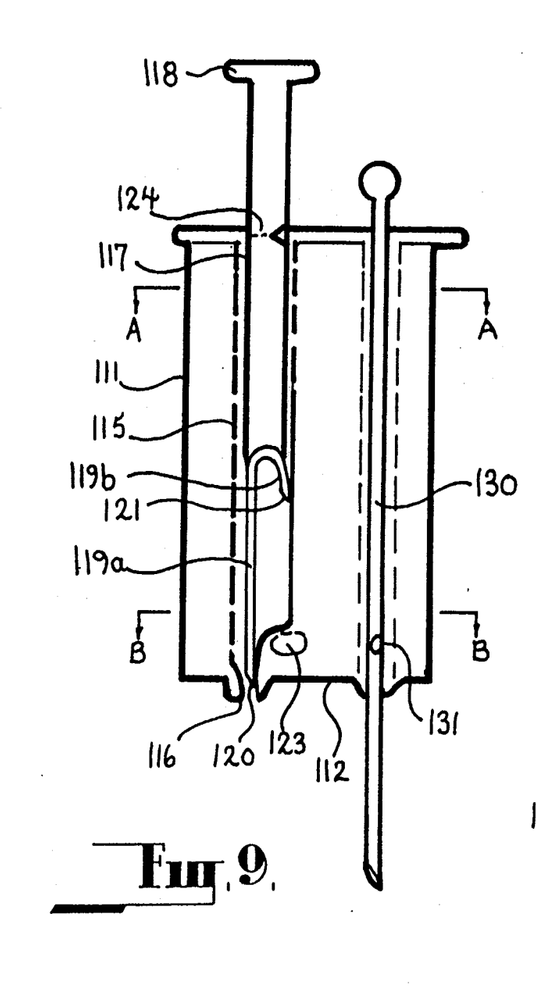
FIG. 9 is a schematic sectional side elevation of the third embodiment.
Figure 10:
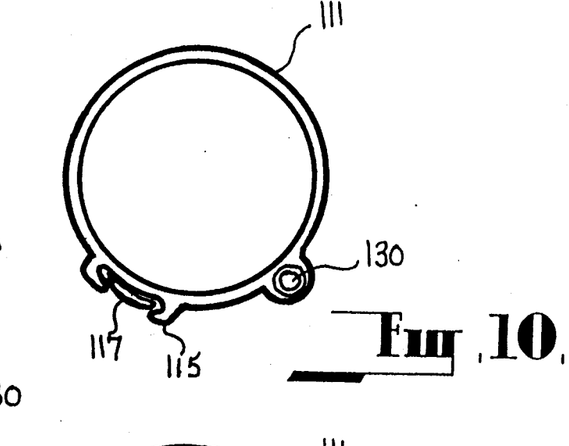
FIG. 10 is a cross-sectional view along the line A—A of FIG. 9.
Figure 11:
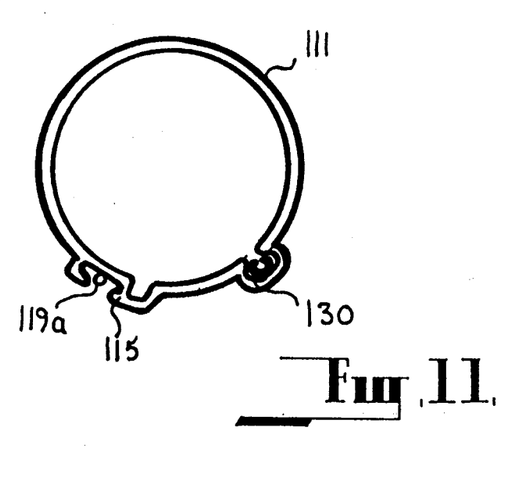
FIG. 11 is a cross-sectional view along the line B—B of FIG. 9.

The third embodiment shown at FIGS. 9, 10 and 11 is of a similar form to the second embodiment shown at FIGS. 6, 7 and 8. Accordingly, corresponding numerals have been used in relation to corresponding components between the second and third embodiments. The difference of the third embodiment from the second embodiment resides in the presence of an additional retractable 130 needle which is co-linear and is provided with a second aperture 131 in its side wall which can be brought into selective engagement with an aperture provided in the wall of the cylindrical body on the needle being moved to an extended position. The second needle 130 can be utilised for the withdrawal of a parenteral agent from an ampoule and on completion of the filling of the chamber of the syringe the second needle can be moved to a position at which the needle 119 is exposed within the body and the first hook shaped needle is brought into engagement with the chamber to allow for the injection of the parenteral medium into the body of a patient.

Figure 12:
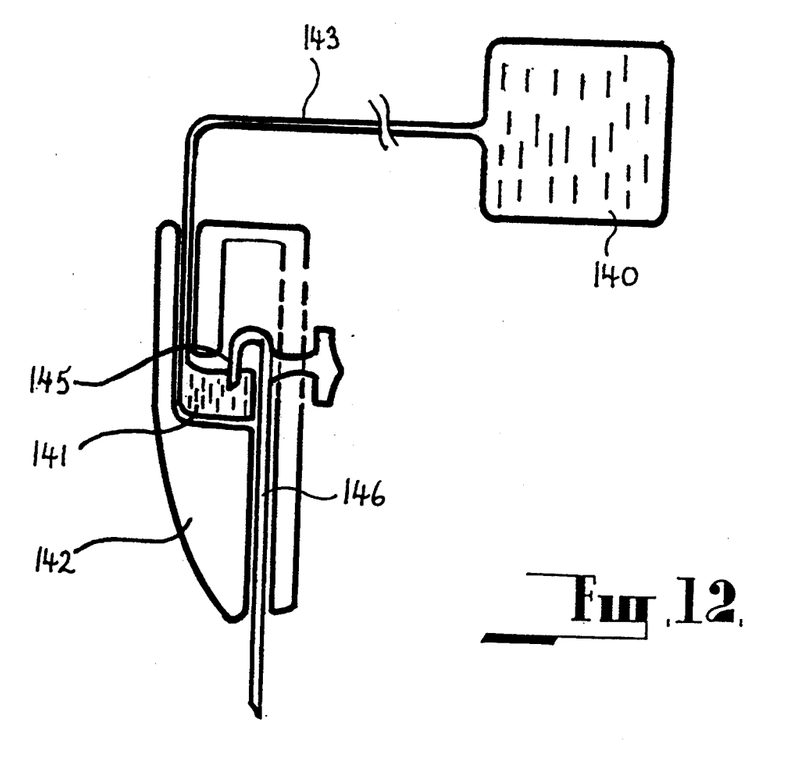
FIG. 12 is a schematic view of the fourth embodiment of the invention with the needle in the second position.
Figure 13:
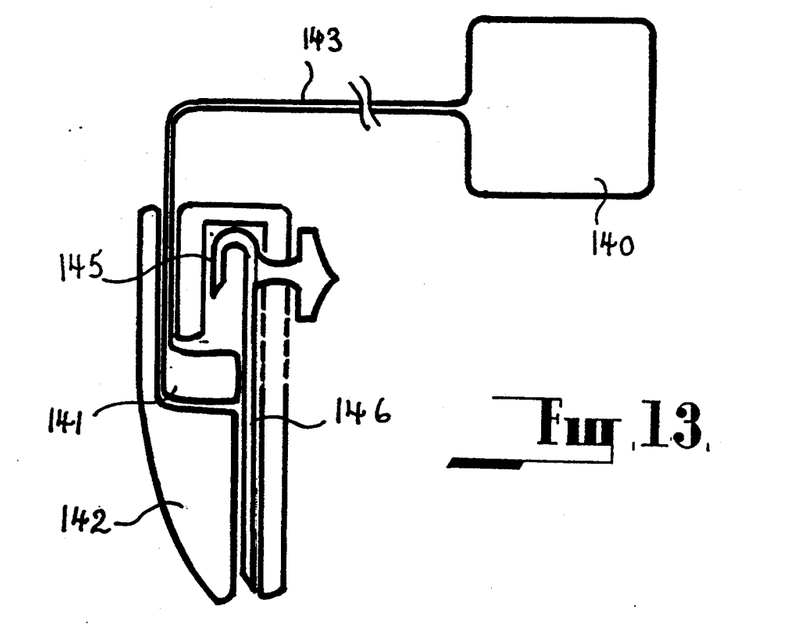
FIG. 13 is a schematic sectional view of the embodiment with the needle in the first position.

The fourth embodiment of FIGS. 12 and 13 comprises a cannula which is substantially similar to that of the first embodiment described in relation to FIGS. 1 to 5 except that the chamber includes a reservoir 140 which is remote from the body of the device and which is in communication with a recess 141 provided in the body 142 of the device through a tube 143. The hook portion 145 of the needle 146 can be brought into selective engagement with the recess 141. It is envisaged that the fourth embodiment would have application in the collection of fluids such as blood from the body of a patient whereby the blood collection bag incorporates the cannula of the embodiment as a unitary component and there is no need for assembly prior to its utilisation.

Figure 14:
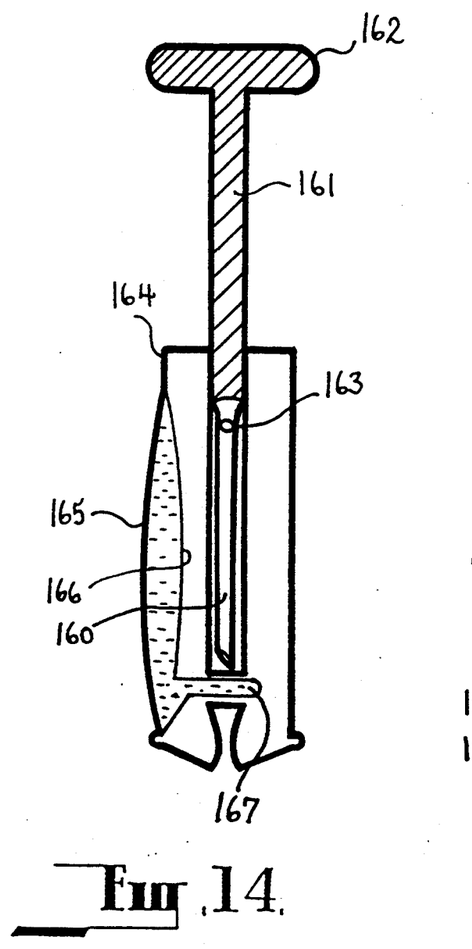
FIG. 14 is a schematic elevation of the fifth embodiment of the invention with the needle in the first position.
Figure 15:
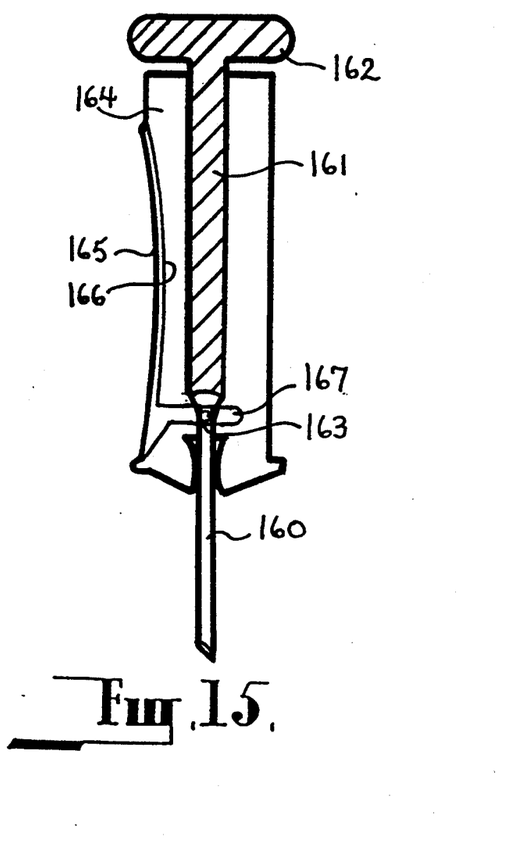
FIG. 15 is a schematic elevation of the fifth embodiment showing the needle in the second position.

The fifth embodiment shown at FIGS. 14 and 15 is directed to an injection device whereby the needle 160 is of a colinear configuration and is received on one end of a rod shaped member 161 having a handle 162 at its outer end. The second aperture 163 of the needle 160 is provided along the length of the needle. As in the case of the first embodiment the chamber is defined between an external face of the body 164 and a laminar element 165 which is bonded around its sides to the external face of the body 164 which is provided with a concave depression 165 and is formed with an extension 167 which extends into the body across the path of the needle as it moves from its first position at which the needle is fully accommodated within the body to its second position at which the needle is exposed. On movement of the needle from the first position to the second position it will pierce the extension 166 and on attaining its second position the second aperture will come into communication with the interior of the chamber to allow for the expulsion of the parenteral agent from the chamber through the hollow needle.

Figure 16:
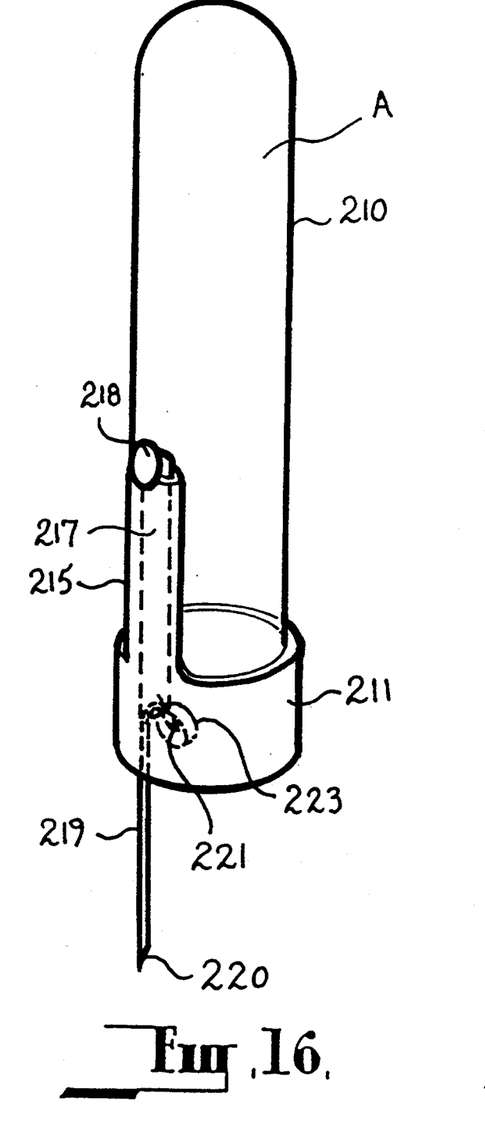
FIGS. 16 and 17 are a schematic representation of a sixth embodiment of the invention.
Figure 17:
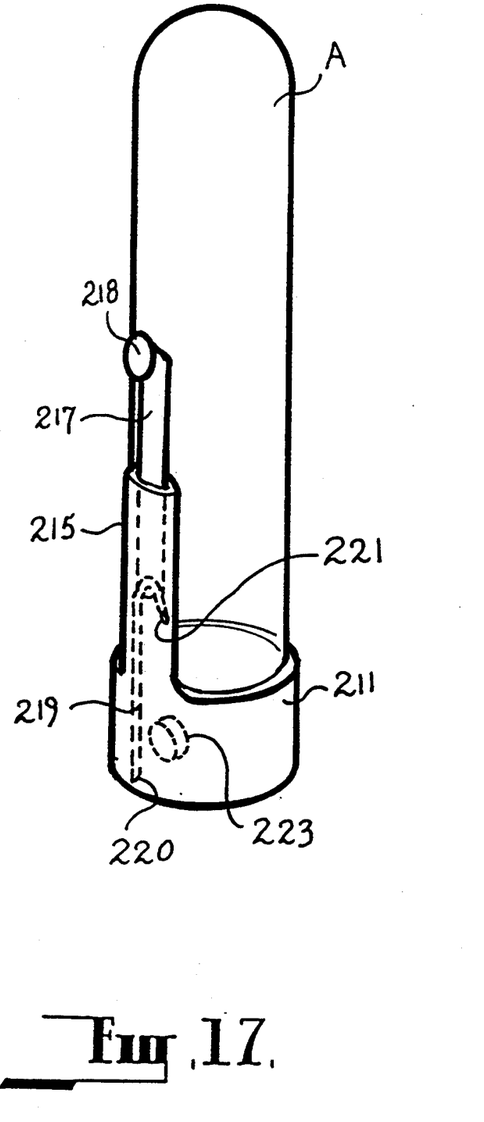

The sixth embodiment of the invention shown at FIGS. 16 and 17 relates to a sampling device. The sixth embodiment is similar in a very general form to the second embodiment shown at FIGS. 6, 7 and 8 except that the chamber A is defined by a container 210 which has an open end closed by a cap 211. The cap 211 has a socket which will sealingly receive the open end of the container 210 and is formed with a tubular sub housing 215. The sub housing 215 accommodates a needle body having a rod-shaped member 217 with a handle 218 at its outer end, which supports a hook shaped needle 219 at its other end. As in the second embodiment of FIGS. 6, 7 and 8 the hooked needle is slidably movable between a first position shown at FIG. 17 at which the one end 220 of the needle is within the tubular sub housing 215 and a second position shown at FIG. 16 at which the needle extends from the tubular body 215. The cap 211 is formed with a transverse wall 223 which is pierced by the other end 221 of the hooked needle as it approaches the second position to provide communication between the chamber A and the one end 210 of the needle.

In use the chamber A is evacuated and if the one end of the needle is caused to enter the body of a patient just prior to the needle being moved fully into the second position body fluids will be drawn into the chamber on the needle being moved fully to the second position.

It should be appreciated that the scope of the present invention need not be limited to the particular scope of the embodiment described above.

I claim:

1. A parenteral device comprising a body, the body having a chamber which is stationary relative to the body, a hollow needle extending generally in a forward to rearward direction and having a forward main straight portion that terminates in a pointed one end with a first aperture at said pointed one end, the needle being supported in the body for slidable movement between a first position and a second position wherein said first position comprises said needle being fully accommodated in the body, said second position comprises said one end of said needle extending beyond the body, said needle having a rearward offset portion that terminates in an offset end, which offset end has a second aperture, which second aperture rearward of the first aperture, wherein the body is formed with a separating wall which sealingly separates the needle from the chamber; the combination of the offset end and the separating wall being arranged such that the offset end is directed generally in the same direction as the forward main straight portion, with the separating wall being located such that said needle in said slidable movement from the first position to the second position orients the offset end for piercing the separating wall that separates the chamber from the needle and, after the offset end does pierce the separating wall, causing the second aperture to be brought into open communication with the interior of the chamber when in the second position, to allow flow of fluid between the chamber and first aperture.

2. A parenteral device as claimed at claim 1 wherein the needle is retained in a substantially enclosed space in the body when in the first position.

3. A parenteral device as claimed in claim 1 further comprising an initially deactivated retention means that becomes activated when the needle is moved into the second position, for preventing, once activated, movement of the needle in the direction from its first position to its second position, whereby the retention means retains the needle in the first position on movement of the needle from the second position to the first position, said retention means preventing the subsequent movement of the needle from the first position to the second position.

4. A parenteral device as claimed in claim 3 wherein said retention means comprises an abutment to be engaged by the needle on movement towards or away from its second position to cause deformation of the needle, which deformation allows movement of the needle from its second position to its first position but prevents subsequent movement of the needle from its first position to its second position.

5. A parenteral device as claimed in claim 1 wherein the offset portion is formed as a continuation of the forward main straight portion whereby said needle has a substantially hook shaped configuration.

6. A parenteral device as claimed in claim 5 further comprising:
an initially deactivated retention means that becomes activated when the needle is moved into the second position, for preventing once activated movement of the needle in the direction from its first position to its second position, whereby the retention means retains the needle in the first position on movement of the needle from the second position to the first position, said retention means preventing the subsequent movement of the needle from the first position to the second position;
wherein said retention means comprises an abutment to be engaged by the needle on movement towards or away from its second position to cause deformation of the needle, which deformation allows movement of the needle from its second position to its first position but prevents subsequent movement of the needle from its first position to its second position; and,
wherein an attitude of the offset portion is varied on engagement with the abutment such that the offset, portion engages the body on movement in the direction to the first position to prevent further movement of the needle in the opposite direction from the first position to the second position.

7. A parenteral device as claimed in claim 1 wherein said device comprises a cannula.

8. A parenteral device as claimed in claim 7 wherein the chamber has a main portion remote from the body.

9. A parenteral device as claimed in claim 8 further comprising means for connecting the chamber to a second chamber remote from the body.

10. A parenteral device as claimed in claim 1 wherein the parenteral device comprises a syringe where the chamber is substantially cylindrical and slidably and sealingly receives a plunger whereby movement of the plunger causes a variation in volume of the chamber.

11. A parenteral device as claimed in claim 1 wherein said chamber is sealed.

12. A parenteral device as claimed at claim 1 wherein the separating wall is resiliently flexible.

13. A parenteral device as claimed at claim 12 wherein the separating wall is resiliently biased to a minimum volume position of the chamber.

14. A parenteral device as claimed at claim 12 wherein the separating wall is resiliently biased to a maximum volume position of the chamber.

* * * * *